United States Patent [19]
Mizori et al.

[11] Patent Number: 5,973,166
[45] Date of Patent: *Oct. 26, 1999

[54] METHOD FOR THE PREPARATION OF MALEIMIDES

[75] Inventors: Farhad G. Mizori, La Mesa; Stephen M. Dershem, San Diego, both of Calif.

[73] Assignee: The Dexter Corporation, Windsor Locks, Conn.

[ * ] Notice: This patent issued on a continued prosecution application filed under 37 CFR 1.53(d), and is subject to the twenty year patent term provisions of 35 U.S.C. 154(a)(2).

[21] Appl. No.: 09/033,432

[22] Filed: Mar. 2, 1998

[51] Int. Cl.$^6$ .................. C07D 207/448; C07D 307/60; C07C 57/03
[52] U.S. Cl. ..................... 548/548; 549/262; 562/595
[58] Field of Search ............. 549/262; 562/595; 548/548

[56] References Cited

U.S. PATENT DOCUMENTS

| | | | |
|---|---|---|---|
| 2,444,536 | 7/1948 | Searle | 260/313 |
| 5,087,705 | 2/1992 | Okada et al. | 548/458 |
| 5,371,236 | 12/1994 | Kanayama et al. | 548/521 |
| 5,484,948 | 1/1996 | Yanaguchi et al. | 548/549 |

OTHER PUBLICATIONS

Kita et al., Journal of Applied Polymer Science, 63(3), pp. 363–368, Jan. 1997.
Coleman et al., "Reaction of Primary Aliphatic Amines with Maleic Anhydride" Journal of Organic Chemistry, 24:135 (1959).
Kita et al., The Chemical Society of Japan 12:971–976 (1995).

*Primary Examiner*—Johann Richter
*Assistant Examiner*—Dominic Keating
*Attorney, Agent, or Firm*—Gray Cary Ware & Freidenrich; Stephen E. Reiter

[57] ABSTRACT

In accordance with the present invention, there are provided improved methods for the preparation of maleimide monomers. This new method for the synthesis of maleimides is clearly superior to those documented in the prior art. Furthermore, the invention method utilizes materials with reduced toxicity, thus the overall process has a minimal impact on the environment. Thus, in accordance with the present invention, it has been discovered that certain amine salts can be successfully used to replace the polar, aprotic solvents cited in the prior art for the cyclodehydration of maleamic acids. The use of these salts provides competitive reaction times and product yields relative to results obtained with the polar, aprotic solvents. These salts have the advantage of having no vapor pressure and, therefore, have no possibility to co-distill with the water produced by the cyclodehydration reaction. Furthermore, such salts can be tailored to have desirable solubility characteristics (i.e., soluble in the refluxing azeotropic solvent, but insoluble at room temperature) that permit their easy removal from the reaction product. Such salts are not destroyed during the cyclodehydration reaction and, therefore, can be efficiently recycled again and again.

18 Claims, No Drawings

METHOD FOR THE PREPARATION OF MALEIMIDES

FIELD OF THE INVENTION

The present invention relates to synthetic methods for the preparation of organic compounds, especially maleimides, by the cyclodehydration of maleamic acids.

BACKGROUND OF THE INVENTION

Maleimides are considered to be high performance reactive monomers. The most useful members of this family are the bismaleimides (i.e., reactive monomers containing two maleimide functional groups per molecule). The maleimide function is very reactive and can be cured homogeneously via free radical or anionic mechanisms to yield a polymer linked through succinimide residues. The maleimide group is also a potent dienophile and is capable of reacting via a Diel's Alder mechanism with suitable dienes (or diene precursors such as benzocyclobutenes) to yield polymeric materials. The carbon-carbon double bond in the maleimide group is considered to be very electron deficient and has been observed to form perfectly alternating copolymers via a charge transfer mechanism with electron rich monomers (e.g., cyclo-olefins and vinyl ethers). Furthermore, aliphatic maleimide compounds have recently been shown to be capable of uncatalyzed photopolymerization. Finally, the maleimide group is a very useful reactant in the "ene reaction" and thus bismaleimdes can be used as vulcanizing agents for polyunsaturated polyolefins and rubbers.

The synthesis of maleimide compounds is typically accomplished in two steps. The first step involves the generation of an N-substituted maleamic acid by the direct reaction of a primary amine and maleic anhydride. The second step is the cyclodehydration of the maleamic acid to form the maleimide functional group. The overall scheme for the preparation of maleimide compounds is shown in scheme 1.

Scheme 1

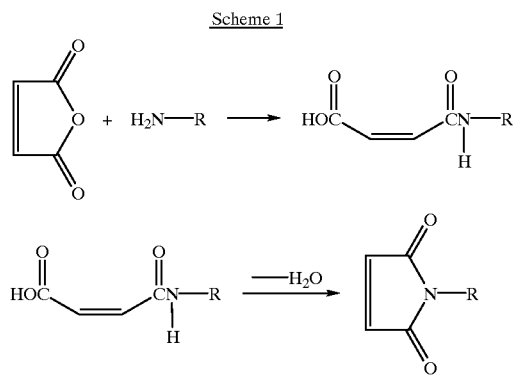

The formation of the maleamic acid is very facile and can usually be accomplished in quantitative yield. It is advisable, however, that the amine be slowly added to a solution containing a stoichiometric excess of the maleic anhydride (this precaution avoids the potential "Michael addition" of the amine across the carbon-carbon double bond of the maleamic acid).

Cyclodehydration of maleamic acid can be accomplished in a number of ways. For example, the use of a chemical dehydrating agent, such as acetic anhydride in the presence of sodium acetate, has been a well established method for accomplishing this second synthetic step (see, for example, U.S. Pat. No. 2,444,536). This method has been acceptable for the generation of technical grade versions of many aromatic maleimide compounds. It fails, however, when applied to the preparation of aliphatic maleimide compounds, and is not preferred for the preparation of high purity aromatic maleimides.

Another chemical dehydrating agent, N,N'-Dicyclohexylcarbodiimide (DCC), in combination with an isomerizing alcohol, has been used to effect cyclodehydration of amic acids to maleimides (see Martin, et al., U.S. Statutory Invention Registration H424, 1988). This method can be used to efficiently make both aliphatic and aromatic maleimides. Unfortunately, the DCC dehydrating agent is very expensive and is also a severe contact allergen for human skin.

Direct thermal cyclodehydration of maleamic acid can be accomplished by heating to a temperature in the neighborhood of 200EC. Unfortunately, this approach is impractical because polymerization of the resulting maleimide would be impossible to avoid under such extreme conditions. Thermal cyclodehydration can be accomplished at lower temperatures by the use of azeotropic distillation in the presence of an acid catalyst. The use of an azeotropic solvent permits the efficient removal of the water co-product as it forms, thereby driving the reaction toward the desired maleimide.

Suitable azeotropic solvents include cyclohexane, benzene, toluene, ethylbenzene, xylenes, cumene, chlorobenzene, butylbenzene, diethylbenzene, mesitylene, and the like. Toluene is considered to be the most desirable of these since it boils at 110EC at atmospheric pressure and is generally an adequate solvent for the amic acid at reflux temperatures. Cylcohexane, as well as the other aliphatic solvents mentioned above, are all much weaker solvents and are usually incapable of dissolving the amic acid. Benzene, which has a lower boiling point than toluene, is considered to be a human carcinogen and is therefore undesirable in any industrial process. The other aromatic solvents noted above have higher normal-atmospheric-pressure boiling points than toluene and thus might be expected to allow for reduced reaction times. However, the higher boiling points of these solvents also can promote thermal isomerization of the maleamic acid to the more thermodynamically stable trans (fumaramic acid) structure, as shown in scheme 2.

Scheme 2

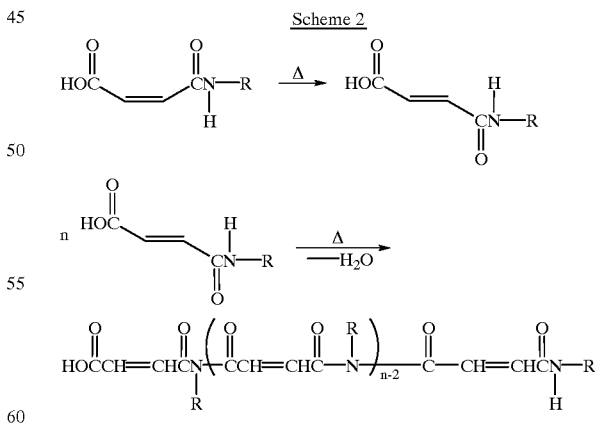

Dehydration of the fumaramic acid to a polyamide, instead of the desired maleimide, represents a serious side reaction that limits the usefulness of the higher boiling azeotropic solvents (see, for example Coleman, et al., Journal of Organic Chemistry, 24:135 (1959)). It would, of course, be possible to use any of the higher boiling solvents as a reaction medium under diminished pressure in order to conduct the reaction at a lower temperature.

Even with the use of toluene as the azeotropic dehydration solvent, poor yields and impractically long reaction times typically result. A significant improvement in both the yield and reaction time can be realized by the incorporation of a polar, aprotic solvent into the reaction mixture. Several polar, aprotic solvents, including dimethylformamide, dimethylacetamide, acetonitrile, N-methylpyrrolidone, dimethylsulfoxide and sulfolane have been claimed to be useful (see, for example, U.S. Pat. Nos. 5,484,948 and 5,371,236, incorporated herein by reference). The most useful of the polar, aprotic solvents is dimethylformamide. Presumably, the presence of the polar aprotic solvent facilitates the reaction by increasing the polarity of the reaction medium. The maleimides of both aromatic and aliphatic amines can be obtained in good yield through the use of these polar, aprotic co-solvents in combination with an azeotropic solvent.

The use of polar aprotic co-solvents does, however, present some problems. These solvents are completely miscible with the azeotropic solvents, making them difficult to remove from the reaction mixture. In addition, polar aprotic solvents generally have high boiling points, requiring higher temperatures and longer evaporation times (than would be required for the azeotropic solvent by itself) for complete removal during work-up of the maleimide product. An exception, acetonitrile, which does have a low boiling point, is impractical because it co-distills without phase separating from the water generated by the dehydration reaction, and cannot therefore remain in the reaction mixture throughout the process. The use of longer and higher temperature evaporation conditions increases the risk of polymerization of the maleimide product.

Polar, aprotic solvents could be removed through aqueous washings, but doing so would create a hazardous and potentially environmentally damaging waste stream. The polar, aprotic solvents, in addition to their own inherent toxicity, are noted for their ability to carry toxic solutes directly into the bloodstream upon contact with human skin. Furthermore, dimethylformamide and dimethylacetamide are subject to hydrolysis and are therefore partially destroyed during the cyclodehydration reaction.

There is, therefore, a need in the art for a viable substitute for the polar, aprotic solvent-containing media used in the thermal cyclodehydration of maleamic acids for the synthesis of maleimides. This and other needs are addressed by the present invention, as will become apparent to those of skill in the art upon review of the specification and appended claims.

BRIEF DESCRIPTION OF THE INVENTION

In accordance with the present invention, we have developed an improved method for the preparation of maleimide monomers. This new method for the synthesis of maleimides is clearly superior to those documented in the prior art. Furthermore, the invention method utilizes materials with reduced toxicity, thus the overall process has a minimal impact on the environment.

Thus, in accordance with the present invention, it has been discovered that certain amine salts can be successfully used to replace the polar, aprotic solvents cited in the prior art for the cyclodehydration of maleamic acids. The use of these salts provides competitive reaction times and product yields relative to results obtained with the polar, aprotic solvents. These salts have the advantage of having no vapor pressure and, therefore, have no possibility to co-distill with the water produced by the cyclodehydration reaction. Furthermore, such salts can be tailored to have desirable solubility characteristics (i.e., soluble in the refluxing azeotropic solvent, but insoluble at room temperature) that permit their easy removal from the reaction product. Such salts are not destroyed during the cyclodehydration reaction and, therefore, can be efficiently recycled again and again.

DETAILED DESCRIPTION O THE INVENTION

In accordance with the present invention, there are provided methods for the preparation of maleimides, said method comprising subjecting an N-substituted maleamic acid in suitable reaction medium to dehydration conditions, wherein said reaction medium comprises a water-immiscible diluent capable of forming an azeotrope with water, said diluent containing an effective amount of a polarity modifying component and an acid catalyst.

N-substituted maleamic acids contemplated for use in the practice of the present invention can be derived from a primary monoamine, a primary diamine or a primary triamine. Thus, primary amines contemplated for use herein include those having the structure:

wherein:

R is a monovalent, divalent or trivalent straight chain or branched chain hydrocarbyl, substituted hydrocarbyl, oxygen-containing hydrocarbyl, substituted oxygen-containing hydrocarbyl, aromatic, substituted aromatic, alkyl-substituted aromatic, substituted alkyl-substituted aromatic radical having in the range of about 10 up to about 500 carbon atoms, and x is 1, 2 or 3, depending on whether R is monovalent, divalent or trivalent.

Exemplary monovalent primary amines contemplated for use herein include stearyl amine, behenyl amine, eicosyl amine, isoeicosyl amine, aniline, benzylamine, cyclohexylamine, cyclopentylamine, methylamine, ethylamine, propylamine, butylamine, pentylamine, hexylamine, octylamine, decylamine, dodecylamine, tetradecylamine, hexadecylamine, octadecylamine, oleylamine, ethanolamine, n-propanolamine, i-propanolamine, butanolamine, aminobenzoic acid, alanine, glycine, and the like.

Exemplary primary diamines contemplated for use herein include diamines such as:

$H_2N—(CH_2)_4—O—(C_3N_3)—[O—(CH_2)_4]_2—NH_2$, wherein $—(C_3N_3)—$ is a 2,4,6-trisubstituted 1,3,5-triazine;

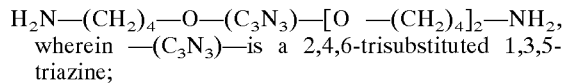

wherein —Ar— is a 1,3-disubstituted phenyl ring;

a C-36 dimer amine, including:

$H_2N—(CH_2)_9—CH(C_8H_{17})—CH(C_8H_{17})—(CH_2)_9—NH_2$, and cyclic isomers thereof;

optionally hydrogenated α,ω-diamino polybutadienes;
optionally hydrogenated α,ω-diamino polyisoprenes;
optionally hydrogenated α,ω-diamino poly[(1-ethyl)-1,2-ethane];
2-methyl-1,5-pentanediamine;
trimethyl-1,6-hexanediamine;

Versamine 551, Versamine 552; and the like.

A presently preferred diamine contemplated for use herein is a C-36 dimer amine, including:

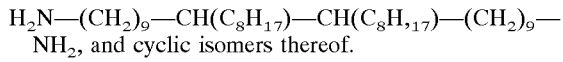, and cyclic isomers thereof.

Diluents contemplated for use herein are water immiscible organic media typically having a boiling point high enough to promote the desired cyclodehydration reaction, without being so high as to promote a significant level of product loss due to undesired polymerization of the maleimide as formed. Suitable diluents typically have a boiling point in the range of about 80-155EC.

Examples of suitable diluents include alkanes (e.g., 2,2,4-trimethylpentane, heptane, octane, and the like), cycloalkanes (e.g., cyclohexane and substituted cyclohexanes), aromatic hydrocarbons (e.g., benzene, toluene, ethylbenzene, xylene, cumene, and the like), halogen-substituted derivatives thereof (e.g., chlorobenzene), and the like.

In accordance with the present invention, it has been discovered that salts of primary, secondary, and tertiary amines, as well as quaternary ammonium compounds, can be used to facilitate the cyclodehydration of amic acids. Polarity modifying components contemplated for use herein can be described by the structure:

wherein:
R' is a monovalent, divalent or trivalent straight chain or branched chain hydrocarbyl, substituted hydrocarbyl, oxygen-containing hydrocarbyl, substituted oxygen-containing hydrocarbyl, aromatic, substituted aromatic, alkyl-substituted aromatic, substituted alkyl-substituted aromatic radical having in the range of about 10 up to about 500 carbon atoms, y is 1, 2, 3 or 4, and A is the anionic portion of the polarity modifying component.

While not wishing to be bound by theory, it is presently believed that these salts increase the polarity of the reaction medium and thus solvate and stabilize ionic intermediates present in the reaction path leading from amic acids to maleimides.

Presumably, any salt could be used provided that it is at least partially soluble in the azeotropic diluent at reflux. Preferably, the salt should be miscible with the azeotropic diluent at reflux. It is of note that this miscibility is often enhanced by the presence in the reaction medium of the amic acid itself. More preferably, the salt employed in the practice of the present invention should not have appreciable solubility in the azeotropic diluent at room temperature.

Preferred salts include those where either the amine and/or acid portion of the salt are lipophilic. Salts where both the amine and acid portion of the salt are lipophilic may be useful in instances where the azeotropic solvent itself has very low polarity. Salts where neither the amine nor the acid portion of the salt are lipophilic are generally not useful since they do not have sufficient solubilizing capability for the reactants even at reflux temperatures.

In accordance with the present invention, it has been discovered that properly selected salts will be miscible at reflux in the azeotropic solvent (containing the amic acid), but become insoluble upon cooling of the reaction mixture (containing the azeotropic solvent and the maleimide product). While the added salt becomes insoluble in the reaction medium upon cooling, the maleimide product remains dissolved in the azeotropic diluent. The salt plus acid catalyst mixture can thus be readily removed and recycled by fractionation in a separatory funnel. An alternative to the need to apply the above selection criteria to the salt employed in the cyclodehydration reaction is the instance where either the base or the acid are polymer bound.

Acids that may be used to form the anion for amine or quaternary ammonium salts contemplated for use in the practice of the present invention include mineral acids (e.g., sulfuric, phosphoric, phosphonic, polyphosphoric, and the like), heteropolyacids (e.g., phosphotungstic acid, phosphomolybdic acid, and the like), organic sulfonic acids (e.g., aliphatic and aromatic sulfonic acids such as, for example, benzenesulfonic acid, para-toluenesulfonic acid, para-bromobenzenesulfonic acid, para-nitrobenzenesulfonic acid, ethylbenzenesulfonic acid, methanesulfonic acid, ethanesulfonic acid, propanesulfonic acid, trifluoromethanesulfonic acid, nonafluorobutanesulfonic acid, 2,2,2-trifluoroethanesulfonic acid, and the like), halogenated carboxylic acids (e.g., trichloroacetic acid, dichloroacetic acid, and the like), as well as polymer bound forms of these acids.

Presently preferred acids contemplated for use herein include methanesulfonic, benzenesulfonic, toluenesulfonic, ethylbenzenesulfonic, phosphoric, and phosphonic acids as well as Amberlyst 15 (Rohm and Haas Co.). It is also preferred, but not required, that the same acid used to form the anion for the salt be used as the acid catalyst for the cyclodehydration.

As is readily recognized by those of skill in the art, some acids (as well as amine or quaternary ammonium salts thereof) should be preferably be avoided in the practice of the present invention. These include oxidizing acids such as nitric or perchloric acids, the use of which could result in hazardous redox reactions. Also any of the hydrogen halide acids such as hydrofluoric, hydrochloric, hydrobromic, and hydroiodic should be avoided (since they tend to hydrohalogenate the maleimide carbon-carbon double bond).

As readily recognized by those of skill in the art, an effective amount of polarity modifying component embraces a wide range of values. Typically, the amount of polarity modifying component employed in the practice of the present invention will fall in the range of about 5 parts per hundred, up to about 90 parts per hundred, on a wt/vol basis, relative to the volume of diluent employed. Preferably, the amount of polarity modifying component employed will fall in the range of about 10 parts per hundred, up to about 50 parts per hundred, on a wt/vol basis, relative to the volume of diluent employed, with in the range of about 20 parts per hundred, up to about 40 parts per hundred, on a wt/vol basis, relative to the volume of diluent employed, being the presently most preferred level.

All of the acids identified above for the generation of suitable salt co-catalysts for use herein are also suitable for the role of acid catalyst for the cycloldehydration reaction. The quantity of acid catalyst used in any reaction will typically fall in the range of about 5 up to about 100 equivalent percent of the number of equivalents of reactive amine substrate used. A presently preferred range for the acid catalyst is about 25 up to about 75 equivalent percent. An especially preferred quantity of acid catalyst contemplated for use is approximately 50 equivalent percent acid catalyst, based on the amount of reactive amine being used.

Quaternary ammonium ions contemplated for use herein as cations of a salt co-catalyst according to the invention include symmetric tetra-substituted moieties including tetramethyl, tetraethyl, tetrapropyl, tetrabutyl, tetrapentyl, tetrahexyl, tetraoctyl, and tetrabenzyl substituted ammonium ions, and the like. Also contemplated are asymmetric quaternary ammonium ions, such as, for example, benzyltrimethyl, dibenzyldimethyl, tribenzylmethyl, ethyltrimethyl, diethyldimethyl, triethylmethyl, dodecyltrimethyl, cetylethyldimethyl, octadecyltrimethyl, dioctadecyldimethyl substituted ammonium ions, and the like. Also contemplated for use herein are alkylpyridinium cations such as, for example, methylpyridinium, ethylpyridinium, propylpyridinium, butylpyridinium, pentylpryidinium, cetylpyridinium ions, and the like.

Tertiary amines contemplated for use herein for the formation of salt co-catalysts of cyclodehydration include symmetrically substituted trialkylamines such as, for example, trimethylamine, triethylamine, tripropylamine, tributylamine, tripentylamine, trioctylamine, tribenzylamine, and the like. Asymmetric tertiary amines are also contemplated for use herein, such as, for example, benzyldimethylamine, dimethylaniline, diethylaniline, dimethylethylamine, dimethylpropylamine, dimethylbutylamine, dimethylpentylamine, dimethylhexylamine, dimethyloctylamine, dimethyldecylamine, dimethyldodecylamine, dimethyltetradecylamine, dimethylhexadecylamine, dimethyloctadecylamine, diethylmethylamine, benzyldiethylamine, diethylpropylamine, diethylbutylamine, diethylpentylamine, diethylhexylamine, diethyloctylamine, diethyldecylamine, diethyldodecylamine, diethyltetradecylamine, diethylhexadecylamine, diethyloctadecylamine, methyldipropylamine, and the like.

Other suitable tertiary amines contemplated for use herein include pyridine, 2,6-dimethylpyridine, polyvinylpyridine, and the like.

Secondary amines contemplated for use herein for the formation of salt co-catalysts of cyclodehydration include symmetrically substituted dialkylamines, such as, for example, dicyclohexylamine, dibenzylamine, dimethylamine, diethylamine, dipropylamine, dibutylamine, dipentylamine, dihexylamine, dioctylamine, didecylamine, didodecylamine, ditetradecylamine, dihexadecylamine, dioctadecylamine, and the like. Asymmetric secondary amines are also contemplated for use herein, including N-methylaniline, methylbenzylamine, ethylmethylamine, methylpropylamine, butylmethylamine, methylpentylamine, hexylmethylamine, methyloctylamine, decylmethylamine, dodecylmethylamine, methyltetradecylamine, hexadecylmethylamine, methyloctadecylamine, N-ethylaniline, ethylbenzylamine, ethylpropylamine, ethylbutylamine, ethylpentylamine, ethylhexylamine, and the like. Other suitable secondary amines contemplated for use herein include piperidine, morpholine, polyethylenimine, and the like.

Primary amines contemplated for use in the practice of the present invention include the same amines used for the synthesis of the targeted maleimide, but are not restricted thereto. Such amines include aniline, benzylamine, cyclohexylamine, cyclopentylamine, methylamine, ethylamine, propylamine, butylamine, pentylamine, hexylamine, octylamine, decylamine, dodecylamine, tetradecylamine, hexadecylamine, octadecylamine, oleylamine, Primene JMT (Rohm and Haas), and the like. Additional primary amines which are suitable for use in accordance with the present invention include Versamine 551 or 552 ("dimer diamine"; Henkel), polyaminostyrene, and the like. In addition, monoamines having other functional groups are also contemplated for use herein, such as, for example, ethanolamine, n-propanolamine, i-propanolamine, butanolamine, aminobenzoic acid, alanine, glycine, and the like.

Kita et al. (Journal of Applied Polymer Science, 63(3):363 (1997); and Nippon Kagaku Kaishi, 1995, pg. 971) describe the use of selected amine salts in the preparation of aliphatic maleimides. They demonstrate improved product yields when an amine salt exactly corresponding to the amine being used to make the maleimide is incorporated into the reaction mixture. Kita et al. theorize that the presence of this specific amine salt serves to increase product yield by minimizing the hydrolysis of the amic acid intermediate during cyclodehydration. Kita et al. clearly did not contemplate that the improved yield might instead arise from the contribution that the amine salt makes toward the total polarity of the reaction medium. Also, since the Kita et al. investigation was restricted to aliphatic amines capable of forming maleimides, only primary amines were considered. It is not surprising, therefore, that the general utility of amine and quaternary ammonium salts for thermal cyclodehydration of amic acids was not recognized.

In addition, it is of note that Kita et al. provide no examples for the preparation of bismaleimides. This omission can readily be rationalized on the basis of the anticipated difficulties (according to the Kita et al. model) that might arise if this same approach were used to synthesize a bi-functional maleimide. If, as Kita et al. theorize, hydrolysis of the amic acid is a significant side reaction, then the presence of a diamine salt co-catalyst would result in scrambling the maleimide and salt functionalities. The desired bismaleimide product, in other words, would be contaminated by compounds containing maleimide and amine salt residues in the same molecule. Therefor, based on the Kita et al. model for employing cyclodehydration to produce maleimides, it appears that preparation of a bismaleimide in the presence of a difunctional salt catalyst is a non-viable synthetic option.

Unlike the traditional polar, aprotic solvent-containing media employed in prior art cyclodehydration reactions, where there are only a limited number of possible solvents to choose from, it can readily be seen that the amine and quaternary ammonium salts described for use in the practice of the present invention can be selected from a large universe of possible combinations of suitable anions and cations. The salt and solvent combination thus can be designed to readily separate into two phases upon cooling at the end of the reaction. Such combinations can therefore be used to great advantage for the synthesis and simultaneous purification of certain maleimide compounds. A lipophilic liquid or low melting maleimide product would thus remain dissolved in the upper (organic) phase while any polar impurities would be retained in the lower (salt) phase after the reaction mixture had been cooled.

As readily recognized by those of skill in the art, a variety of standard additives can be included in the reaction mixture, such as, for example, free radical inhibitors, anti-oxidants, and the like.

Dehydration conditions contemplated for use in the practice of the present invention comprise heating the reaction mixture to reflux of the diluent for a time sufficient to azeotropically remove the resulting water. While reaction times can vary widely, typical reaction times fall in the range of about 0.5 up to about 48 hours.

In accordance with another aspect of the present invention, it has been discovered that aliphatic solvents that are otherwise unsuitable for use for cyclodehydration reactions can be used as the azeotropic solvent. Thus, a very low polarity solvent, such as octane, when combined with a suitably lipophilic salt, produces a homogeneous reaction medium with much better solvent power and thermal cyclodehydration rate at reflux than could ever be achieved with the octane alone.

All U.S. and Foreign Patent publications, textbooks, and journal publications referred to herein are hereby expressly incorporated by reference in their entirety. The invention will now be described in greater detail by reference to the following non-limiting examples.

EXAMPLES

For all of the following examples, commercially available reagents were used as received, with no special treatment. The equipment that was used comprise a suitably sized round bottom flask equipped with a stirrer, a pressure equalized dropping funnel, a Dean-Stark trap and a water cooled condenser. The tetraethylammonium tosylate salt employed in each of the following examples is a commercially available product. All of the other salts employed in the following examples were prepared as needed by simply mixing the desired equivalents of the selected amine with an appropriate equivalent excess of a selected acid in toluene. The maleamic acids employed in these procedures are not very soluble in toluene, and neither are the other salts employed hererin. The combination of the two, however, have good solubility. Anywhere from 5–100 mol % of an acid catalyst (based on the number of equivalents of reactive amine substrate charged into the flask) is required to catalyze the reaction. When the reaction has achieved completion, and the maleamic acid has been converted to maleimide, the salt and acid catalyst are no longer soluble, and precipitate out of solution upon cooling. This feature has been found to make the separation and work-up of the product easy. The amine and ammonium salts used in these reactions have been shown to be re-useable.

Example 1

BMI of Bisaniline-M prepared Using Tetraethylammonium Tosylate and Methanesulfonic Acid To a 250 ml round bottom flask was charged 100 ml of toluene, along with 40 g of tetraethylammonium tosylate. To this solution was added 22.0 g (0.224 mol) of maleic anhydride which had been pulverized to a coarse powder. After the maleic anhydride had dissolved, a dropping funnel was attached which contained 34.5 g (0.100 mol) of bisaniline-M dissolved in 50 ml of toluene. The addition was completed over a forty minute period at room temperature. Since the reaction of an amine with maleic anhydride is exothermic, the solution warms up during the addition which further assists the complete dissolution of the bismaleamic acid as it forms. Subsequently, 10.0 g (0.104 mol, 50 mol %) of methanesulfonic acid was added to help catalyze the reaction. The Dean-Stark trap was attached along with the condenser, and the reaction was heated to reflux using a heating mantle. After four hours of refluxing the toluene-salt mixture 4.0 ml of water was collected (theoretical water was 3.6 ml). The extra water collected was a result of some residual moisture present in the tetraethylammonium tosylate. The reaction mixture was allowed to cool to room temperature, and then placed in a separatory funnel. The top layer (toluene plus dissolved BMI) was set aside, while the bottom layer (salt plus acid catalyst) was washed with 2×50 ml portions of toluene. The toluene extracts were combined with the original toluene plus BMI phase, and the toluene was removed using a rotary evaporator under vacuum at 30 torr, followed by mechanical vacuum (approximately 0.5 torr). A viscous oily liquid was obtained, which was recrystallized from a 75:25 mixture of isopropanol/acetone (volume to volume). A total of 38.5 g of a yellow powder was obtained, a 76.4% yield based on the starting mmoles of bisaniline-M. The melting point of the solid was 142–145° C., IR (KBr) 1713 cm$^{-1}$, 1514 cm$^{-1}$, 1398 cm$^{-1}$, 1147 cm$^{-1}$, 837 cm$^{-1}$, 692 cm$^{-1}$.

Example 2

Bmi of 2-methyl-1,5-pentanediamine Prepared Using Tetraethylammonium Tosylate and Methanesulfonic Acid In a 250 ml round bottom flask equipped with a magnetic stirrer and dropping funnel was placed 100 ml of toluene along with 40 g of tetraethylammonium tosylate, and 22.0 g (0.224 mol) of maleic anhydride. A solution of 11.65 g (0.100 mol) of 2-methyl- 1,5-pentanediamine in 50 ml of toluene was added drop-wise over a period of about thirty minutes to form the bismaleamic acid. Methanesulfonic acid 10.0 g (0.104 mol, 50 mol %) was then added. A Dean-Stark trap and condenser were attached and the solution was heated to reflux. A total of 4.2 ml of water (expected 3.6) was collected after an overnight, approximately 16 hours, reflux. The cooled mixture was poured into a separatory funnel and the toluene (top) phase was set aside, while the salt (bottom) phase was washed with 2×50 ml portions of toluene. The toluene washes and original fraction were combined, and rotary evaporated down to a viscous oil. The work-up consisted of extracting the oil with 500 ml of hot tert-butyl methyl ether. Most of this solvent was then allowed to evaporate while being warmed to produce a saturated solution. This saturated solution, upon cooling to room temperature (and subsequently in an ice bath), generated a large volume of solid. The white solid product was collected by vacuum filtration. The product weighed 27.6 g (83.4% of theory) after drying. The melting point of the solid was 88–91° C., IR (KBr) 1705 cm$^{-1}$, 1408 cm$^{-1}$, 1118 cm$^{-1}$, 844 cm–1, 696 cm$^{-1}$.

Example 3

N-Phenyl-Maleimide Prepared Using Tetraethylammonium Tosylate and Methanesulfonic Acid In a 250 ml round bottom flask was placed 100 ml of toluene along with 20 g of tetraethylammonium tosylate, and 11.0 g (0.112 mol) of maleic anhydride. A solution of 9.54 g (0.102 mol) of aniline dissolved in 50 ml of toluene was then added drop-wise over a period of about thirty minutes. Subsequently, 5.0 g (0.052 mol, 50 mol %) of methanesulfonic acid was added and the reaction was set up as before with a Dean-Stark trap and condenser. After 45 minutes of reflux at 110° C. the theoretical 1.8 ml of water was collected. Heating was allowed to continue for a total of two hours to assure a complete reaction. A total of 2.2 ml of water was collected by the end of this two hour period. The mixture was cooled and placed in a separatory funnel; the toluene (top) phase was set aside while the salt plus acid (bottom) phase was washed with 2×50 ml of toluene. The toluene washes and original toluene fraction were combined and the toluene was removed under vacuum using a rotary evaporator. A very yellow crystalline product is obtained, which was recrystallized from a 90:10 (volume to volume) mixture of isopropanol/water. After drying in the oven at 70° C. for 4 hours, 16.7 g of product was obtained, 94.2% yield. The melting point of the solid is 89–90° C., IR (KBr) 1709 cm$^{-1}$, 1394 cm$^{-1}$, 1145 cm$^{-1}$, 831 cm$^{-1}$, 696 cm$^{-1}$.

Example 4

BMI of Trimethyl-1,6-hexanediamine Prepared Using Tetraethylammonium Tosylate and Methanesulfonic Acid Into a 250 ml round bottom flask equipped with a magnetic stirrer and dropping funnel was added 100 ml of toluene, 40 g of tetraethylammonium tosylate, and 22.0 g (0.224 mol) of maleic anhydride. A solution of 16.0 g (0.101 mol) of trimethyl-1,6-hexanediamine dissolved in 50 ml of toluene was then added dropwise to the stirred contents of the flask. As in the preceding examples 10.0 g (50 mol %) methanesulfonic acid was added and the solution was brought up to reflux in an assembly equipped with a Dean-Stark trap and a condenser. Following approximately 24 hours of reflux, 4.2 ml of water was collected (expected 3.6 ml). Again two phases were formed, the top, toluene phase containing the product was decanted off, while still hot. The salt-acid layer was washed with 2×50 ml of hot toluene. The toluene extracts were combined, and rotary evaporated down to a tan colored solid. The product is recrystallized from tert-butyl methyl ether, 22.98 g of a white powder was collected (72.3% percent of theory). The melting point of the solid was 84–86° C., IR (KBr) 1703 cm$^{-1}$, 1411 cm$^{-1}$, 1159 cm$^{-1}$, 839 cm$^{-1}$, 696 cm$^{-1}$.

Example 5

BMI of Versamine 552 Prepared Using Tetraethylammonium Tosylate and Methanesulfonic Acid Into a 250 ml round bottom flask equipped with a magnetic stirrer and pressure equalized dropping funnel was added 21.5 g (0.219 mol) of maleic anhydride, 100 ml of toluene, and 20 g of tetraethylammonium tosylate. A solution of 54.0 g (0.100 mol) of Versamine 552 (hydrogenated "dimer diamine" from Henkel) dissolved in 50 ml of toluene was then added dropwise over the course of a half hour. Finally, 10.0 g (0.104 mol, 50 mol %) methanesulfonic acid was added, and the mixture was brought to reflux in an assembly as described in the preceding examples. After seven hours of reflux 3.7 ml of water was collected (expected 3.6 ml). The reaction mixture was allowed to cool, and was then placed in a separatory funnel. The toluene layer was set aside, while the salt-acid layer was washed with 2×50 ml of toluene. Again, the toluene washes and original fraction were combined, and rotary evaporated down to a thick brown sludge. The residue remaining in the flask was extracted with approximately one liter of heptane. The resulting solution/suspension was then allowed to settle overnight. This method efficiently separates the desired (lipophilic) BMI from nearly all of the remaining polar impurities. The clear, and nearly colorless, solution of BMI that remains in the upper heptane phase can be recovered at this stage to give approximately an 80% yield. For certain applications an even cleaner product can be obtained through flash chromatography of this heptane solution. In this experiment the flash chromatography (using silica gel as the column packing) option was used and there was obtained, after removal of the heptane, 68 g of a slightly yellow liquid (65% yield). IR (KBr) 1708 cm$^{-1}$, 1406 cm$^{-1}$, 1120 cm$^{-1}$, 827 cm$^{-1}$, 696 cm$^{-1}$.

Example 6

Synthesis of, BMI of Versamine 552 Using Various Amines and Acids

A series of different ammonium salts and acids were used to prepare the bismaleimide of Versamine 552 (Henkel). Quantities of various reagents, and reaction results are summarized in Table 1.

TABLE 1

| COMPONENTS OF SALT | | EQUIVALENTS | | MOL % ACID | REFLUX | |
| --- | --- | --- | --- | --- | --- | --- |
| ACID | AMINE | OF ACID/AMINE | ACID CATALYST | CATALYST | TIME | YIELD |
| Sulfuric acid | Tripropylamine | 1.0/0.5 | Methanesulfonic acid | 50 mol % | 12 hrs | 35% |
| Methanesulfonic acid | Diisopropylamine | 1.0/1.0 | Methanesulfonic acid | 50 mol % | 11 hrs | 62% |
| Methanesulfonic acid | 2,6-Lutidine | 1.0/1.0 | Methanesulfonic acid | 50 mol % | 12 hrs | 61% |
| Methanesulfonic acid | Triethylamine | 1.0/1.0 | Methanesulfonic acid | 50 mol % | 14 hrs | 63% |

All of the yields reported are for the product purified by flash chromatography over silica gel. The yield without this last purification step would have been approximately 20% higher for each of the examples cited above in Table 1. The examples in Table 1 demonstrate that salts from various amine and acid combinations can be used to prepare an aliphatic bismaleimide compound. Superior yields were seen in this series where the acid used to prepare the salt was monobasic.

Example 7

Synthesis of BMI of Versamine 552 Using Tetra-alkyl Quaternary Ammonium Salts

A series of different ammonium salts and acids were used to prepare the bismaleimide of Versamine 552 (Henkel). Quantities of various reagents, and reaction results are summarized in Table 2.

TABLE 2

| SALT | ACID CATALYST | MOL % ACID | REFLUX TIME, hrs | YIELD % |
| --- | --- | --- | --- | --- |
| Tetraethylammonium Tosylate | Methanesulfonic acid | 50 | 16 | 60 |
| Tetraethylammonium | Toluenesulfonic | 50 | 8 | 33 |

TABLE 2-continued

| SALT | ACID CATALYST | MOL % ACID | REFLUX TIME, hrs | YIELD % |
|---|---|---|---|---|
| Tosylate | acid | | | |
| Tetrabutylammonium Tosylate | Methanesulfonic acid | 50 | 10 | 60 |
| Tetrabutylammonium Tosylate | Toluenesulfonic acid | 50 | 12 | 54 |

The examples in table 2 demonstrate that various quaternary ammonium salts and acid combinations can be used to prepare an aliphatic bismaleimide compound. It is believed that the somewhat lower yield seen with the combination of tetraethylammonium tosylate and toluene sulfonic acid was a function of the reduced reaction time used for this run.

While the invention has been described in detail with reference to certain preferred embodiments thereof, it will be understood that modifications and variations are within the spirit and scope of that which is described and claimed.

That which is claimed is:

1. A method for the preparation of a maleimide, said method comprising subjecting an N-substituted maleimic acid in suitable reaction medium to conditions sufficient to promote cyclodehydration thereof,
   wherein said reaction medium comprises a water-immiscible diluent capable of forming an azeotrope with water, said diluent containing an acid catalyst, and an effective amount of a polarity modifying component selected from the group consisting of compounds having an anionic portion and a cationic portion according to the following structure:

$R'_y\!-\!NH_{4-y}{}^+A^-$ wherein:
   R' is a monovalent, divalent or trivalent straight chain or branched chain hydrocarbyl, substituted hydrocarbyl, oxygen-containing hydrocarbyl, substituted oxygen-containing hydrocarbyl, aromatic, substituted aromatic, alkyl-substituted aromatic, substituted alkyl-substituted aromatic having in the range of about 10 up to about 500 carbon atoms,
   y is 2,3 or 4, and
   A is the anionic portion of the polarity modifying component.

2. A method according to claim 1 wherein said diluent has a boiling point in the range of about 80–155° C.

3. A method according to claim 2 wherein said diluent is an alkane, a cycloalkane, an aromatic hydrocarbon or halogen-substituted derivative thereof.

4. A method according to claim 3 wherein said diluent is heptane, octane, 2,2,4-trimethylpentane, cyclohexane, benzene, toluene, ethylbenzene, xylene, cumene or chlorobenzene.

5. A method according to claim 1 wherein y=4.

6. A method according to claim 1 wherein y=3.

7. A method according to claim 1 wherein y=2.

8. A method according to claim 1 wherein said anionic portion of said polarity modifying component is derived from an acid selected from a mineral acid, a heteropolyacid, an organic sulfonic acid or an halogenated carboxylic acid.

9. A method according to claim 1 wherein said acid catalyst is a mineral acid, a heteropolyacid, an organic sulfonic acid or an halogenated carboxylic acid.

10. A method according to claim 9 wherein said mineral acid is sulfuric acid, phosphoric acid, phosphonic acid or polyphosphoric acid.

11. A method according to claim 9 wherein said heteropolyacid is phosphotungstic acid or phosphomolybdic acid.

12. A method according to claim 9 wherein said acid is a polymer-bound sulfonic acid.

13. A method according to claim 9 wherein said organic sulfonic acid is benzenesulfonic acid, para-toluenesulfonic acid, para-bromobenzenesulfonic acid, para-nitrobenzenesulfonic acid, ethylbenzenesulfonic acid, methanesulfonic acid, ethanesulfonic acid, propanesulfonic acid, trifluoromethanesulfonic acid, nonafluorobutanesulfonic acid, or 2,2,2-trifluoroethanesulfonic acid.

14. A method according to claim 9 wherein said halogenated carboxylic acid is trichloroacetic acid or dichloroacetic acid.

15. A method according to claim 1 wherein said dehydration conditions comprise reflux in said diluent and azeotropically removing the resulting water.

16. A method according to claim 15 wherein said reflux is maintained for in the range of about 0.5 up to about 48 hours.

17. A method according to claim 1 wherein in the range of about 5 up to about 100 mol % acid catalyst is employed, relative to the amount of maleamic acid to be converted.

18. A method according to claim 1 wherein an effective amount of said polarity modifying component falls in the range of about 5 parts per hundred, up to about 90 parts per hundred, on a wt/vol basis, relative to the volume of diluent employed.

* * * * *

UNITED STATES PATENT AND TRADEMARK OFFICE
CERTIFICATE OF CORRECTION

Page 1 of 1

PATENT NO. : 5,973,166
DATED : October 26, 1999
INVENTOR(S) : Mizori et al.

It is certified that error appears in the above-identified patent and that said Letters Patent is hereby corrected as shown below:

<u>Column 13,</u>
Line 43, following "aromatic" please insert -- group --.

Signed and Sealed this

Nineteenth Day of March, 2002

Attest:

JAMES E. ROGAN
*Director of the United States Patent and Trademark Office*

*Attesting Officer*